United States Patent [19]

Bertoni

[11] 4,455,292

[45] Jun. 19, 1984

[54] RADIOLOGICAL CONTRAST COMPOSITION AND METHODS

[75] Inventor: John M. Bertoni, San Antonio, Tex.

[73] Assignee: Board of Regents, the University of Texas System, Austin, Tex.

[21] Appl. No.: 365,337

[22] Filed: Apr. 5, 1982

[51] Int. Cl.$^3$ .............................................. A61K 49/04
[52] U.S. Cl. ........................................................ 424/5
[58] Field of Search ............................................ 424/5

[56] References Cited

U.S. PATENT DOCUMENTS

| | | | |
|---|---|---|---|
| 3,360,436 | 12/1967 | Felder et al. | 424/5 |
| 4,101,647 | 7/1978 | Clauss | 424/5 |
| 4,160,015 | 7/1979 | Wiegert | 424/5 |
| 4,192,859 | 3/1980 | Mackaness | 424/5 |

OTHER PUBLICATIONS

Package insert for Amipaque brand of metrizamide marketed by Winthrop Laboratories.
Bertoni, John et al., Abstract 61 "Metrizamide Competitively Inhibits Hexokinase", poster presentation Sep. 9, 1980.
Bertoni et al., Abstract 9, "Metrizamide Competitively Inhibits Brain Hexokinase", delivered as a speech Apr. 30, 1981.
Bertoni et al., "Metrizamide Competitively Inhibits Hexokinase", reprinted from *Transactions of the American Neurological Association*, vol. 105, 1980.
Bertoni et al., "Studies on the Mechanism of Toxicity of Metrizamide", *Biochemical Pharmacology*, 30:1135–1138, (1981).
Bertoni et al., "Asterixis and Encephalopathy Following Metrizamide Myelography", Annals of Neurology 9:366–370 (Apr. 1981).

*Primary Examiner*—Frederick E. Waddell
*Attorney, Agent, or Firm*—Arnold, White & Durkee

[57] ABSTRACT

A radiological contrast composition for cerebrospinal myelography combining an iodo-benzamido-glucopyranose contrast agent and glucose, the glucose being in sufficient quantity to effectively compete in vivo with the contrast agent for brain hexokinase. Intrathecal coadministration of glucose with iodo-benzamido-glucopyranose contrast agents, exemplified by metrizamide, minimizes the central nervous system depression and irritation often associated with the intrathecal injection of the contrast agent alone. Metrizamide and related iodo-benzamido-glucopyranose contrast agents have been shown to interfere with brain glucose metabolism by competitive inhibition of the enzyme hexokinase. The competitive inhibition of hexokinase activity is counteracted by coadministration of a sufficient amount of glucose.

5 Claims, No Drawings

RADIOLOGICAL CONTRAST COMPOSITION AND METHODS

BACKGROUND OF THE INVENTION

The invention relates generally to pharmaceutical compositions and specifically to improved radiological contrast composition for the prevention of toxic side effects associated with the administration of certain iodo-benzamido-glucopyranose x-ray contrast media.

Metrizamide, 2-[3-Acetamido-2,4,6-triiodo-5-(N-methylacetamido) benzamido]-2-deoxy-D-glucopyranose, is widely used as a radiological contrast agent for cerbrospinal myelography. Although metrizamide and chemically related compounds have been regarded as the safest myelographic materials commercially available, temporary confusional state and EEG deterioration occur in about one-third of patients treated. More serious but less frequent central nervous system effects include asterixis, visual, auditory or speech disturbances, grand mal seizures and aseptic meningitis syndrome. These side effects have been recognized for many years, but in 1979 and 1980 several reports of fairly large series of patients with frequent confusion and perceptual aberrations appeared.

Efforts to minimize central nervous system complication and irritation induced by metrizamide and chemically related radiological contrast agents have heretofore involved using the minimum concentration of the contrast agent required for satisfactory contrast; positioning the patient with his head higher than the highest level of the spine; avoiding intracranial introduction of a bolus of contrast composition; administering a small amount of the contrast agent in cervical puncture for studies of the upper spine; injecting the bolus slowly to avoid excess mixing and rapid diffusion in higher cephalad positions; and avoiding abrupt patient movement to prevent excessive mixing of bolus with cerebral spinal fluid. All these manipulative effects are intended to reduce the amount of contrast agent that diffuses to the brain.

Rather than relying on indirect manipulative steps to avoid contrast agent diffusion to brain, there is a need for an inexpensive, reliable, direct mechanism to avoid central nervous system complications induced by the iodo-benzamido-glucopyranose x-ray contrast agents. Following intense pharmacological research into the biochemical activity of the contrast agents, typified by metrizamide, Applicant has discovered that such compounds interfere with glycolysis metabolism in the brain. Specifically, Applicant has demonstrated that metrizamide competes with glucose to inhibit hexokinase activity [see "Competitive Inhibition of Rat Brain Hexokinase by 2-Deoxyglucose, Glucosamine, and Metrizamide," *J. Neurochemistry* 37: 1000 (1981)]. This interference with the utilization of glucose, which normally serves as the obligatory energy source in the brain, may explain some of the depressive effects of intrathecally administered metrizamide and related compounds.

SUMMARY OF THE INVENTION

The present invention provides x-ray contrast compositions and methods for the prevention of certain untoward central nervous system effects associated with the intrathecal administration of iodo-benzoyl-glucosamine and iodo-benzamido-glucopyranose agents. The radiological contrast compositions of the invention include a sufficient amount of glucose in combination with radiological contrast agents which have been shown to be competitive inhibitors of hexokinase, typified by iodo-benzamido-glucopyranose compounds, such that when the composition is administered to a patient there is an adequate amount of glucose to effectively compete in vivo with the contrast agent for brain hexokinase.

Further, the invention provides methods for the co-administration of glucose with hexokinase inhibitor contrast agents to minimize central nervous system side effects attributed by hexokinase inhibition.

DETAILED DESCRIPTION OF PREFERRED EMBODIMENTS

Both glucose and metrizamide as separate and unrelated compositions are routinely used intrathecally in man. For example, it is routine to combine glucose in a 7.5% (w/v) solution with 5% lidocaine for spinal anesthesia prior to abdominal surgery. The glucose provides a density gradient for the incorporated lidocaine such that the anesthetic composition is heavier than the spinal fluid. Consequently, the anesthetic is held by gravity in the desired region of the spinal cord.

Metrizamide, 2-[3-Acetamido-2,4,6-triiodo-5-(N-methylacetamido) benzamido]-2-deoxy-D-glucopyranose, when reconstituted according to certain directions has a specific gravity of 1.184 at body temperature. Since reconstituted metrizamide is hyperbaric with respect to cerebrospinal fluid there is often no need to include density gradients, such as glucose, to control the diffusion of an injected bolus.

Metrizamide is exemplary of a class of iodo-benzamido-glucopyranose compounds useful as x-ray contrast agents having the general structure

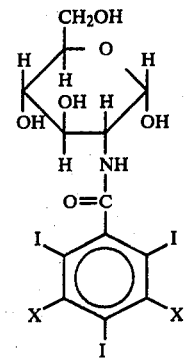

wherein each X independently designates carboxyl, lower acylamino, N-(lower alkyl)-lower acylamino, N-(hydroxy lower acylamino, N-(lower alkyl)-lower acylamino, N-(hydroxy lower alkyl)-lower acylamino, carbamyl, N-(lower alkyl) carbamyl and ureido and pharmaceutically acceptable salts thereof. A lower alkyl is typically an alkyl having 1 to 4 carbon atoms, either straight chained or branched. Other examples of related radiocontrast agents which are encompassed by the scope of this invention include the various iodo-benzoyl-glucosamine derivative compounds which competitively inhibit hexokinase activity typified by but not limited to contrast agents described in Salvesen et al., U.S. Pat. No. 3,702,866; and Wiegert, U.S. Pat. No. 4,160,015.

Metrizamide and related iodo-benzamido glucopyranose contrast agents described above are substituted 2-deoxy-glucose analogs, akin to 2-deoxyglucose and 2-deoxy-2-aminoglucose, which are known inhibitors of hexokinase glycolytic enzymes. Following from structure activity relationships between certain contrast agents and 2-deoxy-glucoses, interference with glucose metabolism was postulated as the mechanism for some of the central nervous system complications associated with contrast agent administration. Accordingly, since metrizamide and related contrast agents compete in vivo with glucose for hexokinase activity, Applicant has demonstrated that providing a sufficient amount glucose to the hexokinase enzyme will substantially counteract interference by the contrast agents.

In accordance with compositions of this invention a radiological contrast media is provided which combines an iodo-benzamido-glucopyranose contrast agent and glucose, the glucose being in sufficient quantity with respect to the contrast agent to effectively compete in vivo with the contrast agent for brain hexokinase.

In a preferred embodiment of the invention metrizamide is combined with glucose. Metrizamide is commercially available as a radiological contrast agent from Winthrop Laboratories and is marketed under the trademark, Amipaque.

The glucose can provided in a powdered or crystalline form in the same container as the powdered metrizamide; or the glucose can be provided in a vial of diluent solution to be mixed with the metrizamide powder prior to administration to the patient. Typically the glucose will be sterilized before mixing with the contrast agent, but it certainly will be sterilized before administration to a patient.

However, since the ratio of radiocontrast agent to glucose should be held within an appropriate range depending upon the degree of hexokinase inhibition exhibited by a particular contrast agent, Applicant prefers for convenience that the glucose be mixed together with the contrast agent as a storage unit and a separate unit of diluent be provided.

The appropriate amount of glucose to be combined with or to be coadministered with a selected iodo-benzamido-glucopyranose contrast agent can be determined by knowing the hexokinase inhibition constant (Ki) for a selected contrast agent. The ratio of the activity of an enzyme to its maximal activity (Vmax) in the presence of competitive inhibitors is given by the following formula: $v/Vmax=[S]/([S]+Km(1+([I]/Ki))$, where [S] is glucose concentration, [I] is inhibitor concentration, Km is the Michaelis constant for glucose utilization of hexokinase, and Ki is the inhibition constant for the contrast agent. With no inhibitor present, glucose utilization by human brain hexokinase is represented by a v/Vmax of 0.99 (the Km for glucose utilization by brain hexokinase is 0.05 mM, and typical spinal fluid contains 4 mM glucose).

For metrizamide in particular, the Ki has been shown to be 2.5 mM with respect to human brain hexokinase. In a routine myelographic procedure, 780 mM (300 mg I/ml) metrizamide is administered. Substituting this variable into the above Michaelis-Menten equation, one finds a v/Vmax of only 0.25. This value represents a significant reduction in glucose utilization. Even if the concentration of metrizamide were diluted tenfold by the time it reached the cerebral surfaces, a v/Vmax of only 0.77 is predicted. Reductions in glucose utilization ranging from 0.6 to 0.7 have been associated with varieties of stupor and coma in humans.

However because metrizamide is a relatively weak competitive inhibitor of glucose, a small increase in glucose concentration can restore hexokinase-glucose utilization to an effective level. It is generally recognized that an objective standard of effectiveness is a metabolic rate which is at least 90% of maximal. By solving for [S] it is calculated that an initial concentration of about 100 mM glucose is needed to counteract the effects of an intrathecal injection of 780 mM metrizamide. Such a molar ratio of 1:7.8, glucose: metrizamide ensures a v/Vmax of at least 0.9. As the metrizamide and glucose are both diluted in the cerebrospinal fluid, the v/Vmax will gradually increase. Generally, selecting a molar ratio ranging from about 1:5 to 1:10, glucose: metrizamide will provide in most routine procedures a sufficient concentration of glucose to effectively compete in vivo with metrizamide for hexokinase activity.

It should be apparent to those skilled in the art in view of this disclosure that the effects of metrizamide are dependent on brain glucose concentration which is in turn dependent on blood glucose concentration. One should keep in mind the various pathological and metabolic conditions in which delivery of endogenous glucose to the brain may be impaired. For example, a marked reduction of blood glucose may occur in women and children who are fasting for several hours prior to a metrizamide myelogram. During the course of a 24 hour fast, the mean blood glucose level may fall to 2.9 mM and levels of as low as 2.4 mM have been noted for fasting children, and 1.9 mM for women. Generally for men, the blood glucose level after fasting is maintained at a higher level ranging for about 3.1–4.4 mM. Under normal conditions, the cerebrospinal and brain glucose levels are roughly one-half to two-thirds of blood glucose.

Since low concentrations of systemic glucose potentiate the effects of a competitive inhibition, it is preferred by Applicant that patients not be in the fasting state for a metrizamide procedure, or should be given glucose intravenously substantially coinciding with the administration of the radiological compositions of this invention.

Further modifications and alternative embodiments of the compositions and methods of this invention will be apparent to those skilled in the art after review of this description. Accordingly, this description is to be construed as illustrative of the preferred embodiments known to Applicant at the time of application and is for the purpose of teaching those skilled in the art the manner of carrying out the invention. For example, although it is preferred that the glucose and radiological contrast agent be co-administered as a single unit, Applicant recognizes that administration of the contrast agent and glucose separately in sequential fashion is an alternative mode. However, Applicant finds this mode objectionable because it necessitates maintaining two aseptic injections and thus increases the risk of infectious contamination. Further, with separate injections of the individual components there is no assurance that the two components will mix well, especially since such a small amount of glucose is needed with respect to the contrast agent. These, and other modifications of the invention will be apparent to those skilled in this art. It is the Applicant's intention that the following claims cover all equivalent modifications and variations as fall within the scope of the invention.

What is claimed is:

1. A method of minimizing in a host the central nervous system complications associated with the intrathecal administration of radiological contrast agents which are competitive inhibitors of hexokinase activity, the method comprising:

coadministering glucose to the host at the substantially the same time as the contrast agent is administered, the glucose being in sufficient quantity to effectively compete in vivo with the contrast agent for hexokinase activity.

2. The method according to claim 1 wherein the glucose and contrast agent are administered together in combination.

3. The method of claim 1 wherein the radiological contrast agent is an iodo-benzoyl glucosamine derivative or pharmaceutically acceptable addition salts thereof.

4. The method of claim 1 wherein the radiological contrast agent is an iodo-benzamido-glucopyranose derivative or pharmaceutically acceptable addition salts thereof.

5. The method of claim 1 wherein the radiological contrast agent is metrizamide or pharmaceutically acceptable addition salts thereof.

* * * * *